United States Patent [19]

Noding

[11] Patent Number: 4,871,430
[45] Date of Patent: Oct. 3, 1989

[54] NOVEL MULTIFUNCTIONAL COMPOUNDS AND ELECTROLYTIC OXIDATIVE COUPLING PROCESS

[75] Inventor: Stephen A. Noding, Brusly, La.

[73] Assignee: The Dow Chemical Company, Midland, Mich.

[21] Appl. No.: 16,595

[22] Filed: Feb. 19, 1987

[51] Int. Cl.$^4$ .......................... C25B 3/00; C25B 11/12
[52] U.S. Cl. ........................................ 204/72; 204/79; 204/80; 204/294
[58] Field of Search ................. 204/59 R, 294, 79, 80, 204/72, 78

[56] References Cited

U.S. PATENT DOCUMENTS

| | | | |
|---|---|---|---|
| 3,759,797 | 9/1973 | Masunaga et al. | 204/59 R |
| 4,405,816 | 9/1983 | Skaletz | 568/592 |
| 4,411,746 | 10/1983 | Degner et al. | 204/59 |
| 4,434,032 | 2/1984 | Baldwin et al. | 204/72 |
| 4,457,810 | 7/1984 | Skaletz | 204/59 |

OTHER PUBLICATIONS

Baizer, Organic Electrochemistry, Marcel Dekker, Inc., N.Y., N.Y., pp. 718–728 (1973).
White, "Synthesis with Electrogenerated Halogens", Journal of Electrochemical Society: Electrochemical Science and Technology, vol. 124, No. 8, 1177–1184, Aug. 1977.

*Primary Examiner*—John F. Niebling
*Assistant Examiner*—Steven P. Marquis
*Attorney, Agent, or Firm*—James M. Pelton

[57] ABSTRACT

A process for electrochemically coupling anions of organic radicals to form multifunctional compounds having the general formula

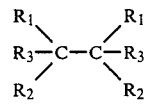

in which $R_1$ and $R_2$ are independently selected from —CN, $CO_2Et$, —$R_4CH_2Et$, —$CO_2R_4$, and —$COCH_3$; $R_3$ is Br, H, or Et, and $R_4$ is $C_{1-12}$ alkyl; and the novel compounds per se.

9 Claims, No Drawings

NOVEL MULTIFUNCTIONAL COMPOUNDS AND ELECTROLYTIC OXIDATIVE COUPLING PROCESS

The present invention relates to a process for producing multifunctional compounds by an electrolytic oxidative coupling process. The process produces both known compounds not heretofore easily available by synthetic chemical processes or ordinary prior art electrochemical processes and novel compounds which were not previously known in the prior art.

Although the electrochemical coupling of radicals formed by anodic oxidation is known, previous processes have problems with selectivity, efficiency and expense. Improvements have been made in selectivity; see for example White "Synthesis with Electrogenerated Halogens", J. Electrochem. Soc.: Electrochemical Science and Technology, Vol. 124, No. 8, 1177–1184, August 1977, which reports yields of malonate esters by indirect electrochemical oxidation ranging from 91 to 98% in some cases with conversions at 90% to 96% and relatively high current densities. However, these reactions occur at the laboratory stage where electrodes of platinum are used which are not satisfactory from the economical point of view for industrial application. Further, even though the best conversion (96%) is with an acetonitrile solvent, platinum electrodes were required because the less expensive graphite electrodes were considerably corroded by the acetonitrile. For this and other reasons, an alcohol solvent, such as methanol, was recommended by White even though conversions and current efficiencies were 25 and 17% lower, respectively.

A review of the oxidative electrochemical coupling of organic anions edited by Baizer, *Organic Electrochemistry*, Marcel Dekker, Inc., New York, N.Y., p. 718 et seq. (1973), shows that acetonitrile is a better solvent than methanol or ethanol, but only when used with platinum electrodes. Nothing regarding the use of graphite electrodes is suggested.

In other electrochemical processes, the problems with graphite anodes are recognized. For example, U.S. Pat. No. 4,411,746 teaches a process for the electrochemical preparation of alkyl-substituted benzaldehydes in which graphite electrode wear is prevented or improved electrode stability is achieved by coating the graphite anodes with metal oxides or with metal carbides using thermal spraying or thermal decomposition. Such anodes are used for producing alkyl substituted benzaldehydes from alkyl benzene derivatives with improved selectivity and increased current yields and, further, for having reduced wear at longer operation life. However, such a process is not an anionic oxidative coupling process. In U.S. Pat. Nos. 4,405,816 and 4,457,810 both to Skaletz the electrochemical process for producing 4,4'-diphenyl ether - dialdehyde - bis-dimethylacetal from di-p-tolyl ether uses anode materials which are only the customary electrochemical anodes, e.g., platinum, lead dioxide, graphite or vitreous carbon. As shown by references above such carbon electrode materials are not suggested for use with acetonitrile solvents in the electrolyte.

U.S. Pat. No. 4,434,032 to Baldwin et al teaches an electrochemical coupling to produce a symmetrical alkanediol by first making a bis-ether from a haloalkanol then electrochemically coupling the bis-ether by removal of the halo group, and finally deetherifying to produce the desired alkanediol. The electrochemical portion of the reaction is carried out in an aqueous ethanol solvent with ammonium chloride anolyte and aqueous ammonium chloride catholyte in a divided cell and using a coiled platinum anode and a cylindrical copper plated copper-bronze wire mesh screen cathode. Graphite electrodes or organic solvents are not suggested.

Thus, there appears to be ample opportunity to provide less expensive and more efficient and selective electrochemical coupling reactions. The present process provides such a process and novel compounds produced by such a process which heretofore were theoretically possible, but not practically available because of equipment and process related limitations.

SUMMARY OF THE INVENTION

The present invention provides a process which comprises the electrochemical oxidation in a solvent of a compound of the formula

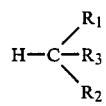

where in $R_1$ and $R_2$ are independently selected from —CN, —CO$_2$Et, —R$_4$CO$_2$Et, —CO$_2$R$_4$, and —COCH$_3$; $R_3$ is selected from H, Br, and Et; and $R_4$ is $C_{1-12}$ alkyl to produce a compound of the general formula

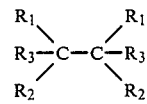

wherein $R_1$, $R_2$ and $R_3$ have the definition given above provided that each $R_1$, $R_2$ and $R_3$ group on the first central carbon atom of the product are the same as on the second central carbon atom and in which the anode is a non-porous graphite anode.

Also, provided is a novel compound prepared by the process of this invention which is a 1,2-dihydro-1,1,2,2-tetracyanoethane. Still further novel compounds are produced when $R_1$ and $R_2$ are different and mixed multifunctional compounds are produced, such as mixed cyanoester compounds, produced from the electrochemical coupling of a cyano acetic acid ester, for example, ethyl or methyl cyanoethanoate to form a 1,2-dihydro-1,2-dicyano-1,2-methoxycarbonyl or ethoxycarbonyl ethane. Several additional novel compounds are known from the first formula above where $R_1$ and $R_2$ attached to the same carbon atom are different and $R_3$ is hydrogen.

DETAILED DESCRIPTION OF PREFERRED EMBODIMENTS

The starting materials for the process of the present invention are generally described by reference to the general formula I given above. In general, derivatives of malonic acid and substituted malonic acids are useful starting compounds in the present invention. The various functional groups which one of skill in the art would consider as typical for compounds of this invention are nitrile and ester groups. The ester groups include alkyl carbon chains having from 1 to about 12 carbon atoms. Various substituents on the central chain carbon atom of the derivatized malonic acid group, in addition to hydrogen, include the ethyl group and bromine. Typically, the starting materials include malonitrile, bromomalononitrile, ethylmalononitrile, dimethyl malonate, dimethyl bromomalonate, dimethyl ethylmalonate, diethyl malonate, dibutyl malonate, dioctyl malonate and didodecyl malonate including the various ethyl and bromo substituted malonic acid esters having from 1 to about 12 carbon atoms in the ester groups. The various mixed ester and cyano group about the novel couple products of this invention herein below.

According to the process of the present invention, the starting material or compound to be oxidatively coupled is added with a solvent to an electrochemical cell of conventional construction. In general, the solvent should be able to dissolve the starting materials and product. It should also have a viscosity which makes the electrochemical cell reaction mixture easily stirable. Solvents which have a dielectric constant greater than about 30 and have an anode limiting voltage greater than about 1.5 volts have been found to be effective. While the solvent can be any polar organic solvent such as methanol or ethanol, it should be understood that the alcohol solvents will not provide the increased selectivity and efficiencies attained with nitrile solvents. Further, where ester groups are present in order to avoid mixed ester groups, if this is desired, the alcohol solvent should be compatible with or have the same number of carbon atoms as the ester groups. For example, when using diethyl malonate as a starting material, ethanol solvent should be employed to avoid mixed ester groups in the final coupled product. For this reason and others, alcohol solvents, while useful, are not as preferred. Typical nitrile solvents include acetonitrile, propionitrile, butyronitrile and benzonitrile with acetonitrile being a most preferred solvent.

The anode materials employed in the electrochemical cell or reactor include inexpensive carbon anodes, usually in the form of graphite. However, the previously cited prior art shows that ordinary graphite anodes several degrade or corrode during reaction. Thus, one skilled in the art would assume that the use of organic solvents, such as the preferred acetonitrile, would likewise affect the carbon anodes of the present invention in the same manner. In complete contrast to the expectations of the skilled artisan, it has been surprisingly found that a non-porous carbon anode provides a highly suitable anode material for use in the present process. Thus, such non-porous anodes, preferrably non-porous graphite anodes, remain uncorroded for considerably longer periods in organic solvents at reaction temperatures and currents than do other carbon materials. For example, according to the prior art porous carbon anodes are only good for less than about eight hours use, whereas a typical non-porous pitch impregnated graphite anode according to the present invention has been in experimental laboratory use intermittently for over one year without degradation. Thus, a non-porous graphite anode is a preferred and highly useful anode material.

The method by which decreased porosity for the graphite anodes is accomplished is not of concern. It is known that graphite electrodes can be impregnated with pitch, such as coal-tar pitch, and form a non-porous electrode material. The pitch acts as a binder, preventing the absorption of the solvent into the graphite pores.

Initially, the formed carbon anodes are heated to graphitize them resulting in an anode structure containing about 20-25% voids and having a density of about 1.62 grams per milliliter (g/ml). The graphitized anode is impregnated with pitch and then dipped in a phenolformaldehyde resin. The resin is cured and the resultant graphite anode has only about 8% voids with none on the surface, a density of about 1.75 g/ml and considerably increased mechanical strength.

Without limiting the operation of the invention to any believed that prior art carbon electrode degradation is caused by the organic solvent being absorbed into the pores of the electrode material. When the reaction occurs, the heat generated swells the solvent causing spalling of the electrode surface which opens more electrode surface area for solvent absorption. The non-porous or electrode binder pitch impregnated graphite anodes used in the present process do not permit absorption of the solvent and thus prevent anode degradation. However, the key to solution of carbon (graphite) anode degradation problem is to understand the mechanism by which it occurs. Without such understanding there is no reason to suggest that any carbon electrode would be useful in the present process much less a non-porous graphite anode.

The amount of binder required should only be that amount sufficient to seal the exterior surface, but impregnation preferably should include the entire anode cross-section so that solvent breakthrough at surface or subsurface mechanical or chemical imperfections does not subvert the non-porous barrier, resulting in corroding or degradation of the binder impregnated anode surface. Typically, the amount of binder is from about 6 to about 10 weight percent based on the total weight of the anode. The preferred binder pitch, as indicated above, is a coal-tar pitch. More preferably the impregnation agent is a mixture of pitch coke and medium hard coke-oven pitch. Pitches are derived from tars which commonly are obtained from destructive distillation of coal, crude oils and other organic materials. Generically, such materials are included in the term bitumen which is a black or dark-colored weight hydrocarbons, of which asphalts, tars, pitches and Sphaltites are typical. Although the type of pitch depends to a certain extent on its source, synthetic pitches are available and produced by mixing or blending natural or processed products together. A preferred type of impregnation pitch is composed of a coal-tar pitch which is a mixture of about 70 weight percent pitch coke and about 30 weight percent coke-oven pitch. Certain pitch impregnated graphite electrodes are commercially employed by various companies in electrochemical preparation of chlorine in chlor-alkali cells. It has heretofore not been suggested to use such anodes in electrochemical anodic oxidative coupling reactions.

The electrolytic cells used in the process of this invention have not been found to require any specific cell configuration. An undivided cell has been satisfactorily employed in the process of the present invention. The cathode can be any conventional material such as stainless steel, nickel, and iron. A platinum cathode could be used, but it would not be economical. The electrolyte can be potassium or sodium iodide with potassium being preferred. Such conventional electrolytes are known in the art. The cell voltage can range from about 4 to about 15 volts per cell depending on the size, configuration and number of cells. Preferably the cell voltage is from 4-7 volts per cell. The current density employed in this process ranges from about 100 to about 300 mA per square inch (15.5 mA/cm² to 46.5 mA/cm²). The reaction temperature can range from about 45° to about 65° C., preferably from about 50° to about 60° C. Good stirring is helpful to maintain contact of the reagents. The reaction is carried out for a period of time sufficient to attain essentially complete reaction. This can be readily calculated based on the amount of reactants. Usually, the reactants are in stoichiometric ratio. The reaction is stopped by turning off the electricity, stopping the stirring and cooling or allowing the reaction mixture to cool. Product work up is conveniently carried out by stripping off the solvent, usually with vacuum, washing the product, separating product from metallics and residue, and washing again to produce the desired material.

The process of the present invention is more particularly illustrated by the following non-limiting examples.

EXAMPLES

According to the process of this invention a number of experiments were carried out to show the nature and scope of the process. In general, the procedure for such experiments included the use of a 500 ml electrochemical cell in which the appropriate electrodes were fitted and the cell was purged with nitrogen. Then 0.01 mole of starting material was added together with solvent and electrolyte. The current was turned on and the reaction was allowed to continue for about 6 hours. Product work up for a non-nitrile containing product included addition of water until a precipitate formed, collecting the solid, and repeatedly washing with tetrahydrofuran. The solid product was then dried, weighed and analyzed by infrared spectrometry. Because the nitrile-containing products are very water soluble, no water was added to the work up procedure for them. Instead the solvent was evaporated and the residue repeatedly washed with small amounts of tetrahydrofuran until the iodine/iodide was removed. The remaining solid was then dried, weighed and stored under dry nitrogen until analysis by infrared spectrometry.

The following table gives the conditions and results of several experiments carried out according to the process of the present invention. In addition, several experiments which are not in accord with this invention are shown for comparison.

TABLE

Electrolytic Coupling of Organic Anions to Produce Multifunctional Compounds

| Ex. No. | Starting Compound | Electrolyte/ Solvent (amount or concentration) | Electrode Anode | Electrode Cathode | Current Density | Voltage (volts) An | Voltage (volts) Cath | Voltage (volts) Cell | Current Efficiency | Product |
|---|---|---|---|---|---|---|---|---|---|---|
| 1 | Diethyl Malonate (DEM) | Potassium iodide/acetonitrile | non-porous graphite | lead (Pb°) | 100 | — | — | 4.5 | >90 | tetraethyl 1,1,2,2-ethane tetracarboxylate |
| 2. | Diethyl Malonate (DEM) | Potassium iodide/acetonitrile | non-porous graphite | platinum | 100 | — | — | 4.1 | >85 | tetraethyl 1,1,2,2-ethane tetracarboxylate |
| 3. | Diethyl Malonate (DEM) | Tetrabutyl/ ammonium iodide (0.5 molar)/ acetonitrile | non-porous graphite | stainless steel | 100 | — | — | 5.7 | 75 | tetraethyl 1,1,2,2-ethane tetracarboxylate |
| 4. | Diethyl Malonate (DEM) | Potassium iodide (0.1 molar)/ acetonitrile | non-porous graphite | platinum | 100 | 1.5 | 4.5 | 6.0 | 90 | tetraethyl 1,1,2,2-ethane tetracarboxylate |
| 5. | Diethyl Malonate (DEM) | Potassium iodide/ ethanol | non-porous graphite | platinum | 100 | 1.5 | 3.5 | 5.0 | 88 | tetraethyl 1,1,2,2-ethane tetracarboxylate |
| 6. | Diethyl Malonte (DEM) | Potassium iodide/ ethanol | non-porous graphite | platinum | 100 | 1.5 | 3.2 | 4.7 | 85 | tetraethyl 1,1,2,2-ethane tetracarboxylate |
| 7. | Diethyl Malonate (DEM) | Potassium iodide/ acetontrile | non-porous graphite | platinum | 250 | — | — | 6.8 | 93 | tetraethyl 1,1,2,2-ethane tetracarboxylate |
| 8. | Malononitrile | Potassium iodide/ acetonitrile | non-porous graphite | platinum | 100 | — | — | >6 | >60 | 1,1,2,2-tetra cyano-ethane (very dark solution after 2 days) |
| 9. | Malanonitrile | Potassium iodide/ acetonitrile | non-porous graphite | lead/tetra fluoroethylene composite | 100 | — | — | 6.0 | <60 | 1,1,2,2-tetra cyano-ethane (cathode |

TABLE-continued

Electrolytic Coupling of Organic Anions to Produce Multifunctional Compounds

| Ex. No. | Starting Compound | Electrolyte/ Solvent (amount or concentration) | Electrode Anode | Electrode Cathode | Current Density | Voltage (volts) An | Voltage (volts) Cath | Voltage (volts) Cell | Current Efficiency | Product |
|---|---|---|---|---|---|---|---|---|---|---|
| 10. | 2,4 Pentandione | Potassium iodide/ acetonitrile | non-porous graphite | platinum | 100 | — | — | 6.0* | 40 | 3,4-diaceto-2,5-hexane-dione (swelling after 2 days) |
| 11. | Ethyl cyano-acetate | Potassium iodide/ acetonitrile | non-porous graphite | platinum | 100 | — | — | >6.0 | <45 | diethyl 2,3-dicyano-succinate |
| 12. | Dimethyl malonate | Potassium iodide/ acetonitrile | non-porous graphite | platinum | 100 | — | — | 6.0 | 95 | tetramethyl 1,1,2,2-ethane tetra-carboxylate |
| Comparative examples | | | | | | | | | | |
| A. | Diethyl malonate | Potassium iodide/ acetonitrille | platinum | platinum | 100 | — | — | 4.1 | 80 | tetraethyl 1,1,2,2-ethane tetra-carboxylate |
| B. | Diethyl malonate | Potassium iodide/ acetonitrile | platinum | lead/tetra fluoroethylene porous cathode with PE-Nb current collector | 100 | — | — | 4.1 | 80 | tetraethyl 1,1,2,2-ethane tetra-carboxylate |

*initial voltage; final cell voltage 8.3v.

From the foregoing experimental data, the present invention can be seen to produce as good a result using nonporous graphite anodes as comparative examples with the same reactants, but using the expensively prohibitive platinum anodes. These results should also be compared with literature results using acetonitrile solvent and porous graphite anodes resulting in the recommendation to use lower yielding alcohol solvents because of porous graphite anode corrosion.

The table above teaches preparation of a series of interesting compounds. Although the ethane tetraester compounds are known per se, it is believed that the 1,1,2,2-tetracyanoethane and the diethyl 2,3-dicyanosuccinate are novel compounds per se. As seen in the above Table these novel compounds are easily prepared by the process of the present invention.

The compounds prepared by the present invention process are useful as detergent builders and intermediates for such. Particularly the tetraethyl 1,1,2,2-ethane tetracarboxylates have been investigated for detergent builder properties. Other of the compounds produced by the present process have properties suitable for use as chelating agents, monomers for polymerization to polymers having functional groups on the polymer backbone and the like.

Having described the novel compounds and process of the present invention, one skilled in the art will be aware of various changes which can be made to the invention within the scope and spirit thereof. Accordingly, the present invention should only be limited to the lawful scope of the appended claims.

I claim:

1. A process which comprises the electrochemical oxidation in a nitric solvent of a compound of the formula

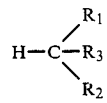

wherein $R_1$ and $R_2$ are independently selected from —CN, —CO$_2$Et, —CO$_2$H, —R$_4$CO$_2$Et, —CO$_2$R$_4$, and —COCH$_3$; $R_3$ is selected from H, Br, and Et; and $R_4$ is $C_{1-12}$ alkyl to produce a compound of the general formula

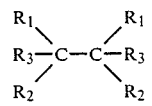

wherein $R_1$, $R_2$ and $R_3$ have the definition given above provided that each $R_1$, $R_2$, and $R_3$ group on the first central carbon atom of the product are the same as on the second central carbon atom and in which the anode is a non-porous graphite anode impregnated with an electrode binder pitch.

2. The process of claim 1 in which said electrode binder pitch is a material selected from coal-tar pitch which is a mixture of about 70 weight percent pitch coke and about 30 weight percent medium-hard coke-oven pitch.

3. The process of claim 1 wherein said electrochemical oxidation is carried out in a solvent selected from acetonitrile, propionitrile, butyronitrile, and benzonitrile.

4. The process of claim 1 wherein said electrochemical oxidation is carried out in an electrolytic cell at a temperature in the range of about 50° to about 60° C.

5. The process of claim 4 wherein the cell voltage ranges from about 4 to about 15 volts and the current density is from about 150 to about 250 mAmps per square inch (23-38 mAMP/cm$^2$).

6. The process of claim 4 wherein the cathode of said cell is selected from stainless steel, nickel, iron and platinum.

7. The process of claim 1 wherein said compound of formula

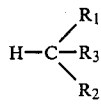

is selected from malonitrile, 2,4-pentanedione, ethyl cyanoacetate, dimethyl malonate, and diethyl malonate.

8. The process of claim 1 wherein said non-porous graphite anode is impregnated with electrode binder pitch, said solvent is selected from acetonitrile and said electrochemical oxidation is carried out in an electrolytic cell at a temperature in the range of about 50° to about 60° C.

9. The process of claim 8 wherein said compound of the formula

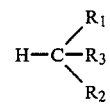

is malonitrile.

* * * * *

UNITED STATES PATENT AND TRADEMARK OFFICE
CERTIFICATE OF CORRECTION

PATENT NO. : 4,871,430

DATED : October 3, 1989

INVENTOR(S) : Stephen A. Noding

It is certified that error appears in the above-identified patent and that said Letters Patent is hereby corrected as shown below:

Column 3, line 11, between "group" and "about" insert -- substituents are also included and more will be described --; Column 3, line 12, "couple" should read -- coupled --.

Column 4, line 10, after "any" add -- particular mode, theory or mechanism of action, it is --; Column 4, line 42, between "dark-colored" and "weight" insert -- cementitious substance and is composed of high molecular --.

In The Claims:

Column 7, Claim 1, line 67, "nitric" should read -- nitrile --.

Claim 7, column 9, line 15, and Claim 9, Column 10, line 15, "malonitrile" should read -- malononitrile --.

Signed and Sealed this

Sixth Day of August, 1991

*Attest:*

HARRY F. MANBECK, JR.

*Attesting Officer*   *Commissioner of Patents and Trademarks*